US012629140B2

(12) United States Patent

Schulz et al.

(10) Patent No.: US 12,629,140 B2

(45) Date of Patent: May 19, 2026

(54) MANUAL SURGICAL INSTRUMENT AND MAIN BODY FOR A MANUAL SURGICAL INSTRUMENT

(71) Applicant: OLYMPUS WINTER & IBE GMBH, Hamburg (DE)

(72) Inventors: Kevin Schulz, Wilstedt (DE); Irina Schmuck, Heide (DE); Bastian Schroeder, Hamburg (DE); Andreas Ruehs, Ahrensburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 327 days.

(21) Appl. No.: 18/120,237

(22) Filed: Mar. 10, 2023

(65) Prior Publication Data

US 2023/0293161 A1 Sep. 21, 2023

Related U.S. Application Data

(60) Provisional application No. 63/319,827, filed on Mar. 15, 2022.

(51) Int. Cl.
*A61B 1/00* (2006.01)
*A61B 17/00* (2006.01)

(52) U.S. Cl.
CPC ................... *A61B 17/00234* (2013.01); *A61B 2017/00296* (2013.01); *A61B 2017/0034* (2013.01); *A61B 2217/007* (2013.01)

(58) Field of Classification Search
CPC .. A61B 2017/00296; A61B 2017/0034; A61B 2217/007; A61B 1/00066; A61B 1/00068; A61B 1/00137; A61B 1/00135; A61B 1/015; A61B 1/307
See application file for complete search history.

(56) References Cited

U.S. PATENT DOCUMENTS

| | | | |
|---|---|---|---|
| 2013/0035553 A1* | 2/2013 | Konstorum | ............ A61B 1/018 600/156 |
| 2014/0318582 A1 | 10/2014 | Mowlai-Ashtiani | |
| 2016/0174819 A1 | 6/2016 | Ouyang et al. | |

FOREIGN PATENT DOCUMENTS

| | | |
|---|---|---|
| DE | 9302891 U1 | 4/1993 |
| EP | 2 537 478 B1 | 1/2014 |
| WO | 2016/122500 A1 | 8/2016 |

\* cited by examiner

*Primary Examiner* — Timothy J Neal
(74) *Attorney, Agent, or Firm* — Oliff PLC

(57) ABSTRACT

A main body for a manual surgical instrument and a manual surgical instrument, in which tools or access articles can be guided in a straightforward way through a channel, and by means of which at the same time a sufficiently large irrigation flow can be delivered through the channel. This is achieved in that two irrigation bores, which extend through a wall of a main body of a manual surgical instrument, are directed onto an upper region of a cross section of a channel running axially through the main body. In this case, the bores are arranged transversely with respect to the channel.

8 Claims, 3 Drawing Sheets

MANUAL SURGICAL INSTRUMENT AND MAIN BODY FOR A MANUAL SURGICAL INSTRUMENT

Figure 1:
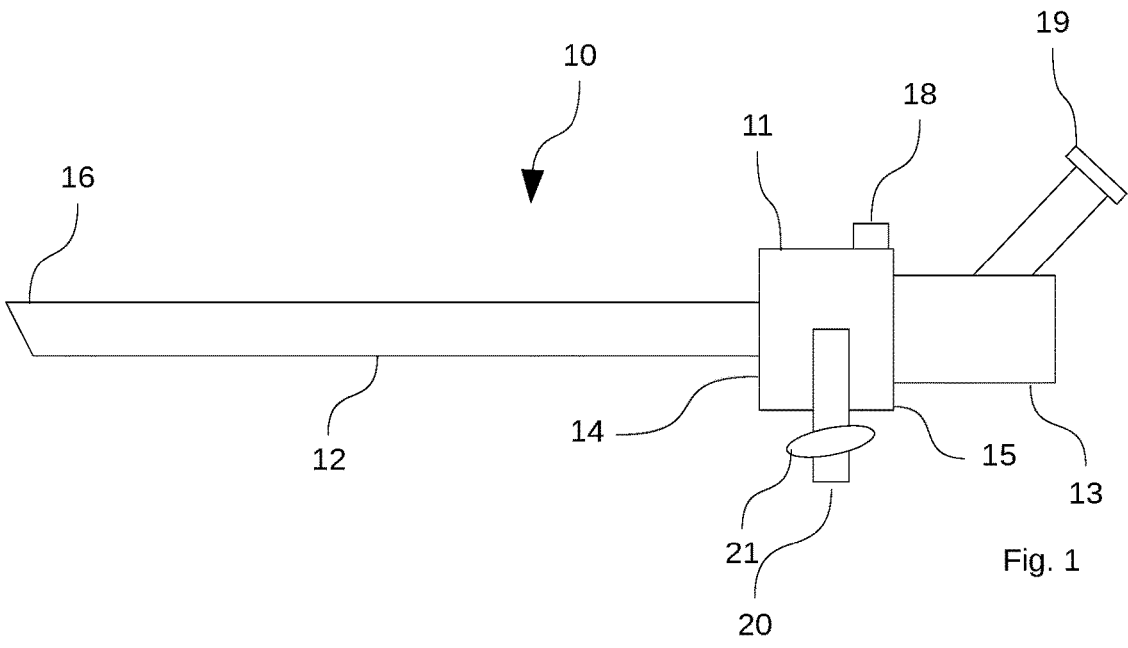

The invention relates to a main body for a manual surgical instrument. The invention furthermore relates to a manual surgical instrument.

For urological applications, as is known, manual surgical instruments, for example endoscopes, cystoscopes and resectoscopes, are used. In some treatments or operations, the region to be treated in the interior of the body of the patient needs to be filled with a liquid. For example, before treatment of the human bladder, the latter is filled with water. When using optical instruments, it is furthermore known for the distal region of the instrument to be irrigated with a liquid during the treatment, in order to provide the best possible viewing conditions for the operator. In these applications, it is important in particular that the flow of liquid through the instrument, in particular through a shaft of the instrument, into the body takes place with a constant and sufficiently high flow speed. For this purpose, in the aforementioned instruments it is provided that two irrigation connections are arranged on a main body of the instruments. Via these irrigation connections, a liquid can be delivered through irrigation bores in the main body into a channel, or into an inner shaft of the instrument. From there, the irrigation liquid can be guided through a shaft, which can be connected to the main body, to the site of the treatment, or into an interior of the human body.

The irrigation bores extend through a wall of the main body and meet the channel laterally. The channel generally has a circular cross section and extends axially through the main body. Through the channel, for example, an optical unit can be pushed from the proximal end to the distal end of the shaft. It is known that a working channel may also extend through the main body, in particular parallel to the channel. This working channel is used for the reception or passage of tools and/or access articles, for example guide wires or electrical lines. The tools or access articles mentioned are guided from the proximal side of the instrument through the working channel of the main body, and optionally through a shaft, to the distal end of the instrument, where they are used for the treatment.

In known applications, the force required for delivering the liquid through the instrument is generated by a hydrostatic pressure. For that purpose, a bag containing the liquid is suspended at a sufficient height above the patient and connected to the irrigation connections by means of tubing. Further regulation of the flow rate can be achieved by valves which are arranged at the connections. The irrigation connections may also be used to clean, or recondition, the instrument after the treatment by using an irrigation liquid. Further components, for example a bridge, a gripping unit, an optical unit plate or the like, may also be connected to the main body of the instrument.

In these instruments, the passage of tools or access articles, for example guide wires, through the working channel of the main body has been found to be problematic. In particular, the access articles may become stuck or caught in the irrigation bores during passage through the working channel. This makes it more difficult to pass the tools and the access articles through to the distal end of the instrument.

On the basis of this, the object of the present invention is to provide a main body for a manual surgical instrument and a manual surgical instrument, in which tools or access articles can be guided in a straightforward way through a channel, and by means of which at the same time a sufficiently large irrigation flow can be delivered through the channel.

For the purpose of achieving this object, a main body has the features of claim 1. It is accordingly provided that two irrigation bores, which extend through a wall of a main body of a manual surgical instrument, are directed onto an upper region of a cross section of a channel running axially through the main body. In this case, the bores are arranged transversely, preferably at an angle of 90°, with respect to the channel. An optical unit or an inner shaft is guided through the upper cross-sectional region of the channel during use of the instrument. The lower cross-sectional region of the channel is separated from the upper cross-sectional region by the optical unit or another inner shaft, which is pushed through the channel. This lower cross-sectional region is also referred to as working channel. Similarly, the upper cross-sectional region may be referred to as optical unit channel. Tools or access articles are guided through the working channel. Owing to the positioning of the irrigation bores, or of the outlets of the irrigation bores, in an upper region of the cross section of the channel, the liquid flowing through the irrigation bores impinges on the optical unit, or the inner shaft which is located inside the channel. The irrigation bores are covered toward the lower region of the cross section of the channel, or toward the working channel, by the optical unit or by the inner shaft. When the tools or access articles are inserted through the working channel in this state, they can no longer become stuck in the irrigation bores. A simple and reliable way of inserting the tool, or the access article, unimpeded into the main body may thereby be provided.

Preferably, the invention furthermore provides that the two irrigation bores form a non-180° angle with respect to one another. Preferably, it is furthermore conceivable that the two irrigation bores form an angle of 175° to 90°, in particular of 170° to 135° or of 160° to 145°, with respect to one another. According to one particularly advantageous exemplary embodiment, the two bores may form an angle of 150° with respect to one another. The effect of this obtuse angle between the two bores is that the irrigation liquid impinges obliquely on an upper region of the tubular optical unit, or of the inner shaft. In this way, on the one hand, it is possible to even more efficiently prevent the access articles from becoming stuck in the bores. On the other hand, the flow behavior of the liquid into the interior of the main body is improved by this oblique impingement of the irrigation liquid on the inner-lying shaft. Ultimately, the irrigation liquid should be guided through the channel to the distal end of the instrument with a high throughput rate. This may, in particular, be achieved by the oblique setting of the irrigation bores relative to a horizontal plane.

Preferably, the invention furthermore provides that the two irrigation bores converge above the working channel and form a space there. This space represents an enlargement of the channel, or of the internal space of the main body. This space or enlargement is formed directly above the optical unit, or the inner shaft, so that the irrigation liquid which flows through the irrigation bores into the interior of the main body has enough room to flow around the optical unit or the inner shaft there and through the channel, in particular through the working channel, to the distal end of the instrument. Ultimately, owing to this enlarged space it is possible to achieve the flow rate required both to irrigate the treatment space in the interior of the patient with the liquid and to free the region around the distal end of the instrument by irrigation.

In particular, it is provided that the space extends in the distal and/or proximal direction inside the main body, at least in sections along the channel. Depending on the embodiment of the main body, the space may be restricted to a very small region or may be formed over a large part of the length of the channel. Ultimately, the main body is also used to guide the aforementioned tools and shafts. The channel, or the working channel, is therefore configured precisely in such a way that it serves as guide for the tools and shafts mentioned and at the same time has a geometry, or a cross section, which is particularly well suited for the inflow of the irrigation liquid.

According to one particularly advantageous exemplary embodiment of the invention, the channel may have an elongate, in particular oval cross section, a rod-shaped optical unit or an inner shaft being guidable through an upper region of the cross section and access articles being guidable through a lower region of the cross section, or the working channel. In this case, it is also conceivable that the elongate cross section of the channel has the contours of an eight. In this embodiment, the optical unit or the inner shaft is guided through the upper region and the access articles are guided through the lower region. Owing to the dimensioning of the cross section, the working channel, or the lower region of the cross section, is ideally shielded from the irrigation bores so that catching of the access articles in the bores is ruled out.

It is furthermore conceivable that the working channel becomes larger in its cross section in the proximal direction of the main body in the manner of a funnel for the purpose of introducing access articles. This funnel-like enlargement is used for improved, or even easier, insertion of access articles into the lower cross-sectional region of the working channel.

A further exemplary embodiment may provide that an outer tube, for example a shaft or the like, can be coupled to a distal end of the main body and further components of the instrument can be releasably coupled to a proximal end. These components may, for example, involve a bridge. This bridge may also comprise at least one channel, in particular a working channel, which is used for the passage of tools, optical units and/or access articles. The bridge may comprise a distal end side by way of which the channel, the space and the funnel-like enlargement of the working channel of the main body are bounded in the proximal direction.

For the purpose of achieving the object mentioned, a manual surgical instrument, in particular an endoscope, a cystoscope, a resectoscope of the like. Accordingly, it is provided that the manual surgical instrument comprises a main body.

Figure 2:
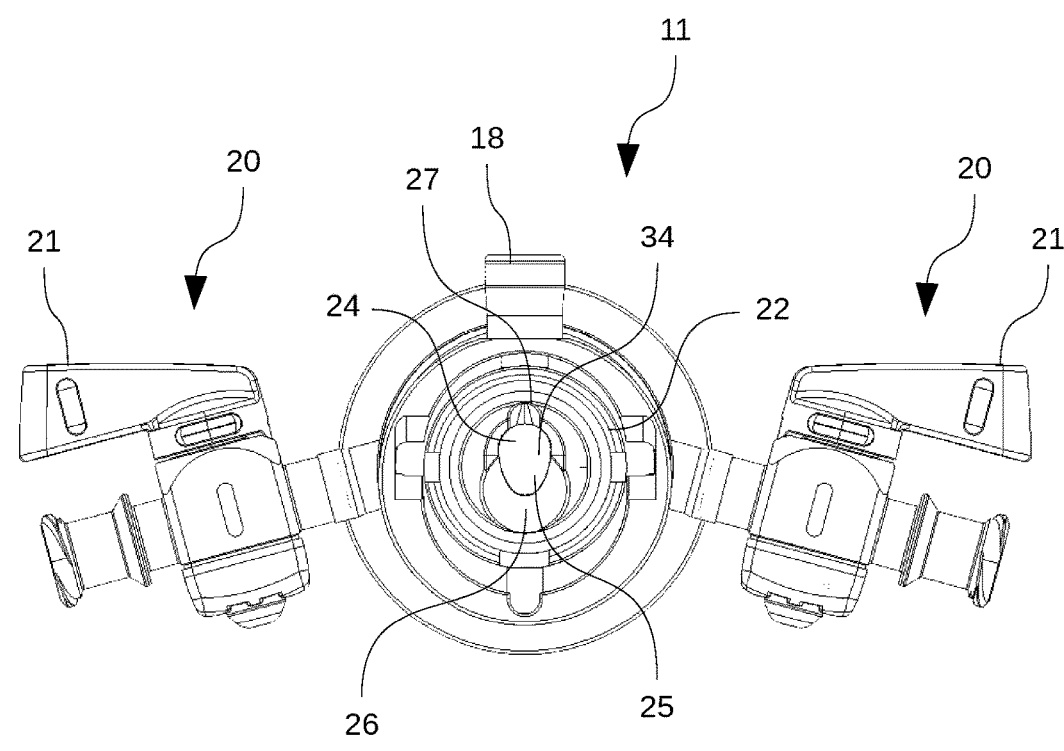
Figure 3:
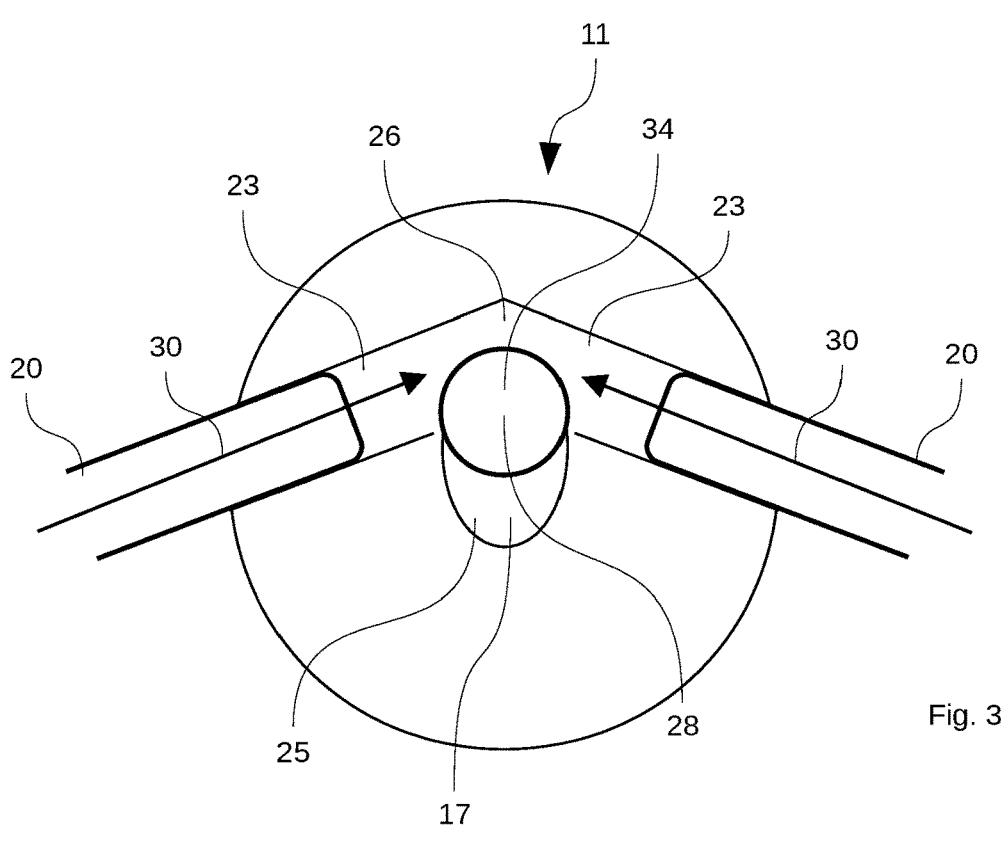
Figure 4:
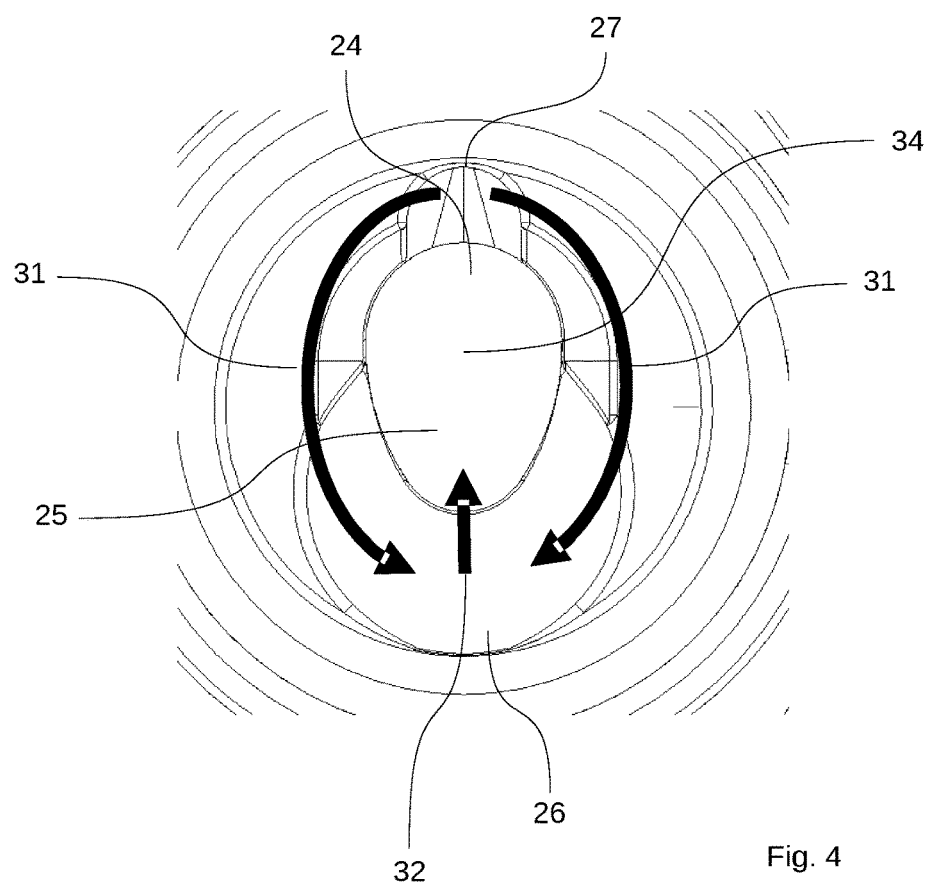
Figure 5:
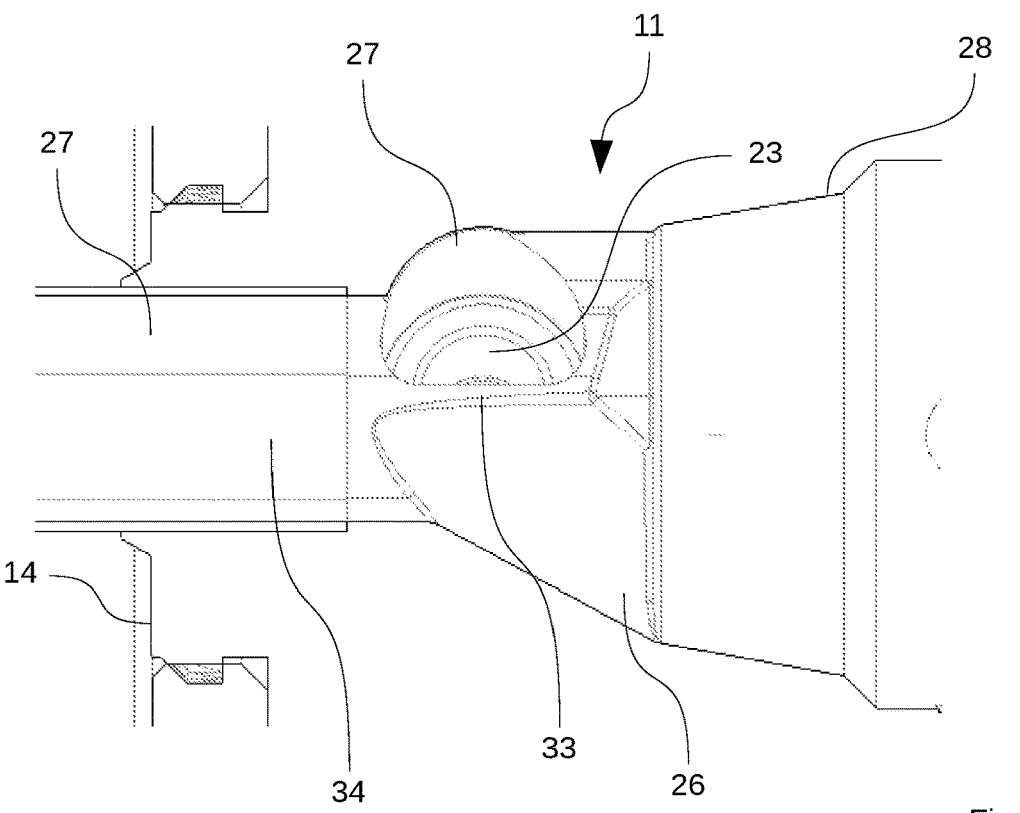
Figure 6:
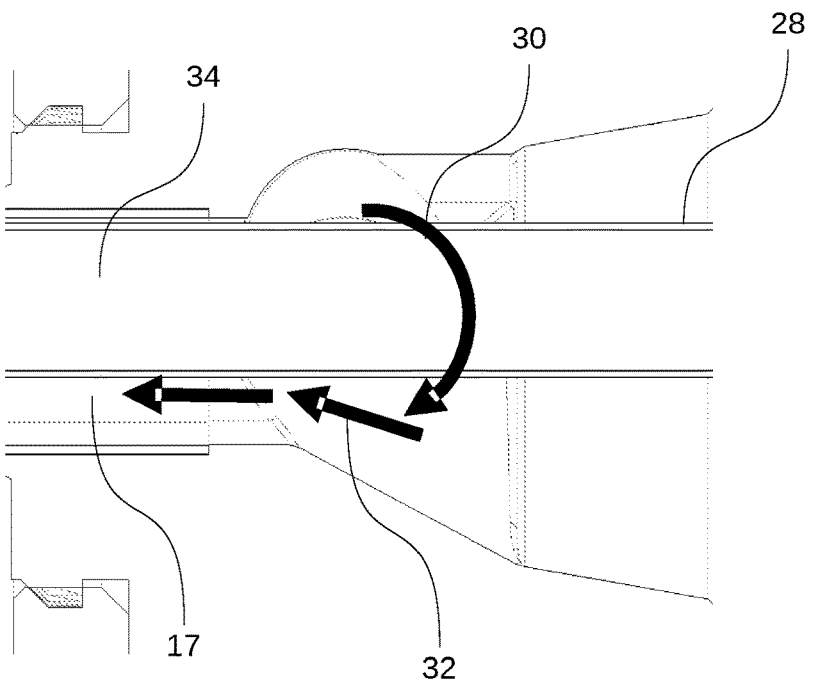

A preferred exemplary embodiment of the present invention will be explained in more detail below with the aid of the drawing, in which:

FIG. 1 shows a schematic representation of a manual surgical instrument,

FIG. 2 shows a sectional representation through a main body of a manual surgical instrument, FIG. 3 shows a schematic representation according to FIG. 2, FIG. 4 shows an enlarged representation of the sectional representation according to FIG. 2, FIG. 5 shows a sectional representation through the main body of the manual surgical instrument, and FIG. 6 shows a further representation of the section according to FIG. 5.

FIG. 1 represents a manual surgical instrument 10 in a highly schematized way. It should expressly be pointed out here that this representation is merely intended to be used for illustration of the subject-matter according to the invention, and any further details as well as real dimensions of a manual surgical instrument have therefore been omitted. For a description of a manual surgical instrument, reference is made to the known prior art.

The instrument 10 outlined here may be an endoscope, a cystoscope, a resectoscope or the like. The essential constituent parts of the instrument 10 are formed by a main body 11, a shaft 12 and a bridge 13. While the shaft 12 can be coupled to a distal side 14 of the main body 11, the bridge 13 can be coupled to a proximal side 15 of the main body 11. In the exemplary embodiment represented in FIG. 1, for example, an actuation means 18 is arranged on the main body 11 in order to release the coupling to the bridge 13. It is furthermore conceivable that, in particular, the shaft 12 and the bridge 13 can be releasably connected to the main body 11 by different types of connection.

During the treatment, the instrument 10 is introduced with the distal end 16 of the shaft 12 in front into the patient's body part to be treated. A tubular channel 34 runs axially inside the shaft 12, the main body 11 and the bridge 13. An optical unit 28, tools or other access articles, for example guide wires or electrical lines, may be guided through this channel 34 to the distal end 16 of the shaft 12. With the aid of these auxiliary means, the operator can carry out the treatment in a targeted manner. On the bridge 13, the exemplary embodiment of the instrument 10 as represented in FIG. 1 comprises an eyepiece 19 which is connected to a glass fiber inside the channel 34 of the instrument 10. Through this eyepiece 19, the operator can look directly into the treatment area. Alternatively, it is also conceivable for a digital camera to be arranged on the bridge 13 in order to represent the treatment on a display screen. Gripping units, mechanical feed-throughs, electrical feed-throughs, bushes for electrical contacting of a tool or the like may furthermore be arranged on the bridge 13.

For many treatments, it is necessary to irrigate the region upstream of the distal end 16 of the instrument 10 with an irrigation liquid. By way of this irrigation, on the one hand the view for the operator can be improved and on the other hand a cavity to be treated in the body can optionally be filled with liquid. The irrigation liquid may be introduced into the working channel 17 via an irrigation connection 20 on the main body 11. In the exemplary embodiment of the instrument 10 as represented in FIG. 1, an irrigation connection 20 is represented in a highly schematized way, laterally on the main body 11. It is quite usual for a further irrigation connection 20 to be arranged on an opposite side of the main body 11. The irrigation liquid may be regulated by means of a cock 21 on the irrigation connection 20. In order to supply a sufficient amount of irrigation liquid, the irrigation connection 20 can be connected to a liquid reservoir. The other end of the irrigation connection 20 is fed through a wall 22 into an irrigation bore 23, which opens into the channel 34. The irrigation liquid flowing through the irrigation connections 20 passes through the irrigation bores 23 into the channel 34 and is delivered by way of corresponding pressure application to the distal end 16 of the shaft 12. Besides use of the irrigation liquid during the treatment, it may also serve for subsequent cleaning or reconditioning purposes.

FIG. 2 represents a section through the main body 11 perpendicularly to the longitudinal axis of the instrument 10. The channel 34 runs centrally through the middle of the main body 11. The cross section of the working channel 17 is oval. While the upper region 24 of the channel 34 is used to receive an inner shaft or an optical unit 28, access articles, for example guide wires or other electrical lines, may be guided through a lower region 25. This lower region 25 is also referred to as a working channel 17. For simple introduction of the aforementioned instruments, the channel 34 has a funnel-like recess 26 in the proximal direction. This recess 26 is shaped in such a way that it delivers the aforementioned tools directly into the working channel 17.

FIG. 2 shows a space 27 above the channel 34. This space 27 is a free volume, which is located above the channel 34 inside the main body 11 and is used for irrigating the optical unit, or for the irrigation liquid to flow into the channel 34. The two irrigation connections 20 are represented laterally with respect to the main body 11. This representation reveals very clearly that the two irrigation connections 20 form an obtuse angle and the irrigation liquid flowing in therefore enters the channel 34 at a corresponding angle. The irrigation liquid therefore does not impinge perpendicularly on the optical unit 28 or the inner shaft (not represented) in the upper region 24 of the channel 34, but does so at an angle which is not 90°. This relative alignment of the irrigation connections 20 is represented in a highly schematized way in FIG. 3 for illustration purposes. This figure likewise represents a cross section through the centrally arranged channel 34 of the main body 11. A rod-shaped optical unit 28 is guided through in the upper region 24 of the channel 34. This region 24 may therefore also be referred to as optical unit channel. This optical unit 28 may be a rod lens system or a glass fiber. Two irrigation bores 23 are fed through the wall 29 of the main body 11 from the sides of the main body 11. Connecting pieces of the irrigation connections 20 are represented schematically in these irrigation bores 23. The irrigation bores 23 are fed into the main body 11 to such an extent that they meet above the channel 34 and form the space 27 there. If the irrigation liquid then enters the irrigation bores 23 through the irrigation connections 20 according to the arrow direction 30, the optical unit 28 is irrigated. Owing to the space 27 extending in the proximal direction, the irrigation liquid can also flow around the optical unit 28 into the lower region 25, or into the working channel 17. From there, the irrigation liquid flows in the distal direction to the distal end 16 of the shaft 12.

One essential feature of the invention is that the irrigation bores 23, or the irrigation liquid, impinge on the upper region 24, or the optical unit 28, in an upper region and converge in the space 27. It has also been found to be particularly advantageous for the optical unit 28, or an inner shaft which is arranged in the upper region 24 of the channel 34, to cover up a direct connection between the working channel 17 and the irrigation bores 23. In this way, the access articles cannot become caught in the irrigation bores 23 during introduction into the working channel 17. Such catching may entail damage to the access article and delays to the preparation for treatment. The working channel 17 is therefore covered by the optical unit 28, or an inner shaft which is guided through the upper region 24. It should again expressly be pointed out that the representation according to FIG. 3 only serves to describe the invention and may differ from the actual embodiment of the main body 11.

FIG. 4 represents an enlargement of a detail of FIG. 2. In this FIG. 4, the flow direction of the irrigation liquid from the space 27 in the direction of the funnel-like recess 26 is represented by the arrows 31. In this case, irrigation liquid in the space 27 flows around the channel 34 in the region of the recess 26. From there, the irrigation liquid flows in the arrow direction 32 through the channel 34, or the working channel 17, in the distal direction of the instrument 10. The irrigation bores 23 are not visible in this sectional representation.

FIGS. 5 and 6 respectively represent sectional representations transversely with respect to the sections of FIGS. 2 and 4 through the main body 11. While an optical unit 28 is guided through the channel 34 in FIG. 6, this optical unit 28 is absent in FIG. 5. In FIG. 5, there is a clear view of the irrigation bore 23 and the adjacent space 27. The funnel-like recess 26, which is separated from the irrigation bore 23 by a web 33, can be seen in the lower region of the main body 11. This web 33 holds the optical unit 28 or an inner shaft in position in the upper region 24 of the channel 34 and prevents access articles (not represented) from becoming caught in the irrigation bore 23. The bridge 13 follows on from the main body 11 in the proximal direction. The shaft 12 may be coupled to the opposite distal side 14.

FIG. 6 shows the way in which the irrigation liquid in the space 27 flows around the optical unit 28 in the arrow direction 30 and flows out from the space 26 in the arrow direction 32 in the distal direction. In this case, the irrigation liquid may also flow between the optical unit 28 and the wall of the working channel 17.

It should expressly be pointed out that that the exemplary embodiment represented in the figures merely represents one possible embodiment of the main body according to the invention. Furthermore, it is conceivable for the claimed main body also to be configured in alternative embodiments.

LIST OF REFERENCE SIGNS 10 manual surgical instrument
11 main body
12 shaft
13 bridge
14 distal side
15 proximal side
16 distal end
17 working channel
18 actuation means
19 eyepiece
irrigation connection
21 cock
22 wall
23 irrigation bore
24 upper region
lower region
26 recess
27 space
28 optical unit
29 wall
30 arrow direction
31 arrow
32 arrow direction
33 web
34 channel

The invention claimed is:
1. A main body for a manual surgical instrument comprising:
    a channel running axially through the main body for passage of tools and access articles;
    an optical unit arranged within the main body; and
    two irrigation bores for connection of a respective irrigation connection, the irrigation bores extending from two opposite sides of the main body through a wall of the main body to the channel, wherein:

the two irrigation bores are aligned with an upper region of a cross section of the channel;

the two irrigation bores form an angle of 170° to 135° relative to one another; and the two irrigation bores converge above the channel and are configured to form a space that is an enlargement of the channel, the space provided between the optical unit and an inner surface of the two irrigation bores where the two irrigation bores converge such that the space is configured to provide sufficient room for irrigation liquid to flow around the optical unit and through the channel that is a working channel to a distal end of the instrument to achieve a required flow rate for irrigation.

2. The main body for a manual surgical instrument as claimed in claim 1, wherein the space extends in a distal and/or proximal direction inside the main body, at least in sections along the channel.

3. The main body for a manual surgical instrument as claimed in claim 1, wherein the channel has an elongated cross section, a rod-shaped optical unit or an inner shaft being guidable through the upper region of the cross section, and the access articles being guidable through a lower region of the cross section.

4. The main body for a manual surgical instrument as claimed in claim 1, wherein the irrigation bores open in the upper region of the cross section.

5. The main body for a manual surgical instrument as claimed in claim 1, wherein a lower region of the channel has a larger cross section than the upper region of the channel such that the lower region of the channel is configured to introduce the access articles.

6. The main body for a manual surgical instrument as claimed in claim 1, comprising a distal end that is configured to be coupled to an outer tube or a shaft, the distal end having a proximal end configured to connect to additional components of the manual surgical instrument.

7. The main body for a manual surgical instrument as claimed in claim 1, wherein a bridge can be coupled to a proximal end of the main body, the bridge comprising at least one channel for the passage of tools, an optical unit and/or the access articles, and the bridge comprising a distal end side by way of which the channel, the space and a funnel-like recess of a working channel of the main body are bounded in the proximal direction.

8. A manual surgical instrument having a main body as claimed in claim 1.

* * * * *